(12) United States Patent
Kelly et al.

(10) Patent No.: US 7,557,098 B2
(45) Date of Patent: *Jul. 7, 2009

(54) 1-ARYL- OR 1-ALKYLSULFONYL-HETEROCYCLYLBENZAZOLES AS 5-HYDROXYTRYPTAMINE-6 LIGANDS

(75) Inventors: Michael Gerard Kelly, Thousand Oaks, CA (US); Derek Cecil Cole, New City, NY (US)

(73) Assignee: Wyeth, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/841,686

(22) Filed: Aug. 20, 2007

(65) Prior Publication Data
US 2008/0200455 A1 Aug. 21, 2008

Related U.S. Application Data

(60) Continuation of application No. 11/324,865, filed on Jan. 4, 2006, now Pat. No. 7,282,495, which is a division of application No. 10/759,595, filed on Jan. 16, 2004, now Pat. No. 7,034,029, which is a continuation-in-part of application No. 10/003,015, filed on Nov. 1, 2001, now abandoned.

(60) Provisional application No. 60/245,118, filed on Nov. 2, 2000.

(51) Int. Cl.
C07D 403/04 (2006.01)
C07D 403/14 (2006.01)
A61K 31/551 (2006.01)

(52) U.S. Cl. .................. 514/218; 540/575; 540/553

(58) Field of Classification Search ............ 540/575, 540/553; 514/218
See application file for complete search history.

(56) References Cited

U.S. PATENT DOCUMENTS

| | | | |
|---|---|---|---|
| 5,849,759 A | 12/1998 | Arnaiz et al. | |
| 5,990,105 A | 11/1999 | Bos et al. | |
| 6,251,893 B1 | 6/2001 | Maddaford et al. | |
| 6,255,306 B1 | 7/2001 | Macor | |
| 6,288,103 B1 | 9/2001 | Faull et al. | |
| 7,087,750 B2 | 8/2006 | Caldirola et al. | |
| 7,282,495 B2 | 10/2007 | Kelly et al. | |

FOREIGN PATENT DOCUMENTS

| | | |
|---|---|---|
| EP | 0 930 302 B1 | 4/2003 |
| WO | WO 96/03400 | 2/1996 |
| WO | WO 9827081 | 6/1998 |
| WO | WO 9902502 | 1/1999 |
| WO | WO 99/65906 | 12/1999 |
| WO | WO 0208178 | 1/2002 |
| WO | WO 0232863 | 4/2002 |

OTHER PUBLICATIONS

Russel MG and Dias R. (Curr. Top. Med. Chem., Jun. 2002; 2(6):643-54).*
Chalmers (TiPS vol. 17, pp. 166-172 Apr. 1996).*
Methvin Issac, et al., (2000) Bioorganic & Medicinal Chemistry Letters, vol. 10, pp. 1719-1721.
Russell MG and Dias R. (2002) Curr. Top. Med. Chem, vol. 2, pp. 643-654.

* cited by examiner

*Primary Examiner*—Kahsay T Habte
(74) *Attorney, Agent, or Firm*—Thomas C. McKenzie; Scott Larsen

(57) ABSTRACT

The present invention provides a compound of formula I and the use thereof in the therapeutic treatment of disorders related to or affected by the 5-HT6 receptor.

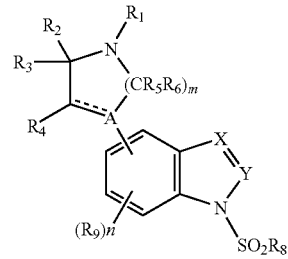

(I)

20 Claims, No Drawings

1-ARYL- OR 1-ALKYLSULFONYL-HETEROCYCLYLBENZAZOLES AS 5-HYDROXYTRYPTAMINE-6 LIGANDS

BACKGROUND OF THE INVENTION

This application is a continuation of U. S. application Ser. No. 11/324,865, filed Jan. 4, 2006, now U.S. Pat. No. 7,282,495, which is a divisional of U.S. application Ser. No. 10/759,595, filed Jan. 16, 2004, now U.S. Pat. No. 7,034,029, which is a continuation-in-part application of U.S. application Ser. No. 10/003,015, filed on Nov. 1, 2001, now abandoned, which claims the benefit of provisional application Ser. No. 60/245,118, filed on Nov. 2, 2000, the entire disclosure of each application is hereby incorporated herein by reference.

Compounds capable of forming 5-HT6 receptor ligands are potentially useful in the treatment of a number of central nervous system disorders such as anxiety, depression, epilepsy obsessive compulsive disorders, migraine, cognitive disorders, sleep disorders, feeding disorders, panic attacks, disorders resulting from withdrawal from drug abuse, schizophrenia, or certain gastrointestinal disorders such as irritable bowel syndrome. Significant efforts are being made to understand the recently identified 5HT-6 receptor and its possible role in neuropsychiatric and neurodegenerative functions. To that end, new compounds which demonstrate a binding affinity for the 5HT-6 receptor are earnestly sought, particularly as potential potent therapeutic agents.

Therefore, it is an object of this invention to provide compounds which are useful as therapeutic agents in the treatment of a variety of conditions related to or affected by the 5-HT6 receptor.

It is another object of this invention to provide methods and compositions useful for the treatment of psychoses (e.g., schizophrenia, anxiety, or depression), motor disorders (e.g., Parkinson's disease), anxiety, depression, obsessive compulsive disorder, attention deficit disorder, or any condition which is known to be related to or affected by the 5-HT6 receptor.

These and other objects and features of this invention will become more apparent by the detailed description set forth hereinbelow.

SUMMARY OF THE INVENTION

The present invention provides a compound of formula I

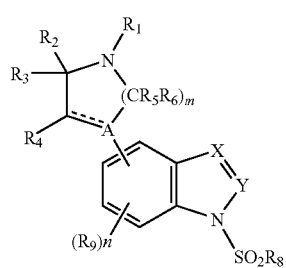

(I)

wherein
A is C, $CR_{10}$ or N;
X is $CR_{11}$ or N;
Y is $CR_7$ or N with the proviso that when X is N, then Y must be $CR_7$;

$R_1$ is H, $C_1$-$C_6$alkylcarbonyl, $C_1$-$C_6$alkylcarbonyloxy or an $C_1$-$C_6$alkyl, $C_1$-$C_6$alkenyl, $C_1$-$C_6$alkynl or $C_5$-$C_7$cycloheteroalkyl group each optionally substituted;
$R_2$, $R_3$, $R_4$, $R_5$ and $R_6$ are each independently H, halogen, OH or an optionally substituted $C_1$-$C_6$alkyl group;
$R_7$ and $R_{11}$ are each independently H, halogen or an $C_1$-$C_6$alkyl, aryl, heteroaryl or $C_1$-$C_6$alkoxy group each optionally substituted;
$R_8$ is an $C_1$-$C_6$alkyl, aryl or heteroaryl group each optionally substituted;
$R_9$ is H, halogen or a $C_1$-$C_6$alkyl, $C_1$-$C_6$alkoxy, $C_1$-$C_6$alkenyl, aryl or heteroaryl group each optionally substituted;
$R_{10}$ is H, OH or an optionally subsituted alkoxy group;
m is an integer of 1, 2 or 3;
n is 0 or an integer of 1, 2 or 3; and
═ represents a single bond or a double bond; or
a pharmaceutically acceptable salt thereof.

The present invention also provides methods and compositions useful in the treatment of central nervous system disorders.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. At present, there are no known fully selective agonists. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders.

Surprisingly, it has now been found that 1-alkyl- or 1-arylsulfonyl-heterocyclylbenzazoles of formula I demonstrate 5-HT6 affinity along with significant sub-type selectivity. Advantageously, said formula I benzazoles are effective therapeutic agents for the treatment of central nervous system disorders associated with or affected by the 5-HT6 receptor. Accordingly, the present invention provides 1-alkyl- or 1-arylsulfonyl-heterocyclylbenzazole compounds of formula I

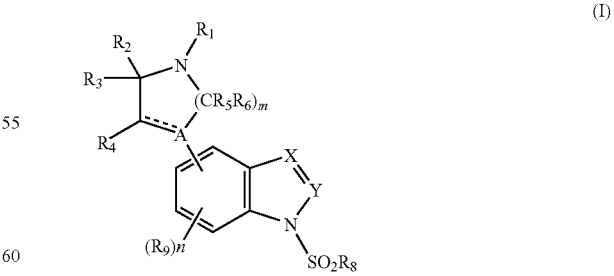

(I)

wherein
A is C, $CR_{10}$ or N;
X is $CR_{11}$ or N;
Y is $CR_7$ or N with the proviso that when X is N, then Y must be $CR_7$;

$R_1$ is H, $C_1$-$C_6$alkylcarbonyl, $C_1$-$C_6$alkylcarbonyloxy or a $C_1$-$C_6$alkyl, $C_1$-$C_6$alkenyl, $C_1$-$C_6$alkynl or cycloheteroalkyl group each optionally substituted;

$R_2$, $R_3$, $R_4$, $R_5$ and $R_6$ are each independently H, halogen, OH or an optionally substituted $C_1$-$C_6$alkyl group;

$R_7$ and $R_{11}$ are each independently H, halogen or an $C_1$-$C_6$alkyl, aryl, heteroaryl or alkoxy group each optionally substituted;

$R_8$ is an $C_1$-$C_6$alkyl, aryl or heteroaryl group each optionally substituted;

$R_9$ is H, halogen or an $C_1$-$C_6$alkyl, $C_1$-$C_6$alkoxy, $C_1$-$C_6$alkenyl, aryl or heteroaryl group each optionally substituted;

$R_{10}$ is H, OH or an optionally subsituted alkoxy group;

m is an integer of 1, 2 or 3;

n is 0 or an integer of 1, 2 or 3; and

≡ represents a single bond or a double bond; or a pharmaceutically acceptable salt thereof.

As used in the specification and claims, the term halogen designates Br, Cl, I or F; the term aryl designates phenyl or naphthyl; and the term cycloheteroalkyl designates a $C_5$-$C_7$cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein Y is NR, O or S and R is H or an optional substituent as described hereinbelow.

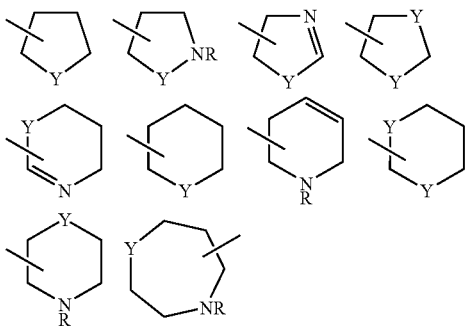

Similarly, as used in the specification and claims, the term heteroaryl designates a $C_5$-$C_{10}$ aromatic ring system containing 1 to 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolinyl, benzothienyl, benzofuranyl, benzisoxazolyl and the like; the term haloalkyl designates a $C_nH_{2n+1}$ group having from one to 2n+1 halogen atoms which may be the same or different; and the term haloalkoxy designates an $OC_nH_{2n+1}$ group having from one to 2n+1 halogen atoms which may be the same or different.

In the specification and claims, when the terms $C_1$-$C_6$alkyl, $C_2$-$C_6$alkenyl, $C_2$-$C_6$alkynl, $C_3$-$C_7$cycloalkyl, cycloheteroalkyl, aryl or heteroaryl are designated as being optionally substituted, the substituent groups which are optionally present include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heteroaryl, cycloheteroalkyl or cycloalkyl groups, preferably halogen atoms or lower alkyl groups. Typically, 0-3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, succinic, fumaric, acetic, lactic, nitric, sulfonic, p-toluene sulfonic, methane sulfonic acid or the like.

Preferred compounds of the invention are those compounds of formula I wherein A is N and m is 2. Also preferred are those compounds of formula I wherein $R_8$ is an optionally substituted phenyl group and $R_1$ is H or a $C_1$-$C_6$alkyl or $C_5$-$C_7$cycloheteroalkyl group each optionally substituted. Further preferred compounds of the invention are those compounds of formula I wherein $R_2$, $R_3$, $R_4$, $R_5$ and $R_6$ are H and n is 0.

More preferred compounds of the invention are those compounds of formula I wherein A is N; m is 2 and $R_1$ is H or a $C_1$-$C_4$alkyl or $C_5$-$C_7$cycloheteroalkyl group each optionally substituted. Another group of more preferred compounds of the invention are those compounds of formula I wherein A is N; m is 2; $R_1$ is H or a $C_1$-$C_4$alkyl or $C_5$-$C_7$cycloheteroalkyl group each optionally substituted; and $R_8$ is an optionally substituted phenyl group.

Among the preferred compounds of the invention are:

1-(phenylsulfonyl)-4-piperazin-1-yl-1H-indole;

1-[(2-bromophenyl)sulfonyl]-4-piperazin-1-yl-1H-indole;

1-[(6-chloroimidazo[2,1-b][1,3]thiazol-5-yl)sulfonyl]-4-piperazin-1-yl-1H-indole;

1-[(3,4-dimethoxyphenyl)sulfonyl]-4-piperazin-1-yl-1H-indole;

1-[(5-chloro-3-methyl-1-benzothien-2-yl)sulfonyl]-4-piperazin-1-yl-1H-indole;

1-[(4-bromophenyl)sulfonyl]-4-piperazin-1-yl-1H-indole;

1-[(5-bromothien-2-yl)sulfonyl]-4-piperazin-1-yl-1H-indole;

1-[(4,5-dichlorothien-2-yl)sulfonyl]-4-piperazin-1-yl-1H-indole;

methyl 4-[(4-piperazin-1-yl-1H-indol-1-yl)sulfonyl]phenyl ether;

4-piperazin-1-yl-1-{[4-(trifluoromethoxy)phenyl]sulfonyl}-1H-indole;

4-(4-benylpiperazin-1-yl)-1-(phenylsulfonyl)-1H-indole;

4-(4-benylpiperazin-1-yl)-1-[(2-bromophenyl)sulfonyl]-1H-indole;

4-(4-benylpiperazin-1-yl)-1-[(6-chloroimidazo[2,1-b][1,3] thiazol-5-yl)sulfonyl]-1H-indole;

4-(4-benylpiperazin-1-yl)-1-[(3,4-dimethoxyphenyl)sulfonyl]-1H-indole;

4-[4-(3-methoxybenyl)piperazin-1-yl]-1-(phenylsulfonyl)-1H-indole;

1-(phenylsulfonyl)-4-[4-(pyridin-4-ylmethyl)piperazin-1-yl]-1H-indole;

1-(phenylsulfonyl)-4-[4-(pyridin-3-ylmethyl)piperazin-1-yl]-1H-indole;

1-[(2-bromophenyl)sulfonyl]-4-[4-(3-methoxybenzyl)piperazin-1-yl]-1H-indole;

1-[(2-bromophenyl)sulfonyl]-4-[4-(pyridin-4-ylmethyl)piperazin-1-yl]-1H-indole;

1-[(2-bromophenyl)sulfonyl]-4-[4-(pyridin-3-ylmethyl)piperazin-1-yl]-1H-indole;

1-(phenylsulfonyl)-5-piperazin-1-yl-1H-indazole;

1-(phenylsulfonyl)-6-piperazin-1-yl-1H-indazole;

1-[(2-bromophenyl)sulfonyl]-6-piperazin-1-yl-1H-indazole;

1-[(4-bromophenyl)sulfonyl]-5-piperazin-1-yl-1H-indazole;

1-[(4-bromophenyl)sulfonyl]-6-piperazin-1-yl-1H-indazole;
1-[(5-bromothien-2-yl)sulfonyl]-5-piperazin-1-yl-1H-indazole;
1-[(5-bromothien-2-yl)sulfonyl]-6-piperazin-1-yl-1H-indazole;
1-[(4-fluorophenyl)sulfonyl]-5-piperazin-1-yl-1H-indazole;
1-[(4-fluorophenyl)sulfonyl]-6-piperazin-1-yl-1H-indazole;
methyl 4-[(5-piperazin-1-yl-1H-indazol-1-yl)sulfonyl]phenyl ether;
1-phenylsulfonyl-4-(4-propylpiperazin-1-yl)-1H-indazole;
1-phenylsulfonyl-4-piperazin-1-yl-1H-indazole;
1-phenylsulfonyl-4-(4-phenethylpiperazin-1-yl)-1H-indazole;
1-phenylsulfonyl-4-[4-(3-phenylpropyl)piperazin-1-yl]-1H-indazole; and the pharmaceutically acceptable salts thereof.

Compounds of the invention may be prepared using conventional synthetic methods and, if required, standard separation and isolation techniques. For example, 4-(piperazin-1-yl)indole compounds of formula II may be readily prepared by the catalytic hydrogenation of the 4-nitroindole precursor of formula III to the corresponding 4-aminoindole of formula IV and reacting said formula IV indole with a bis-alkylating agent such as bis(2-chloroethyl)amine to give the desired formula II intermediate. The reaction is illustrated in flow diagram I.

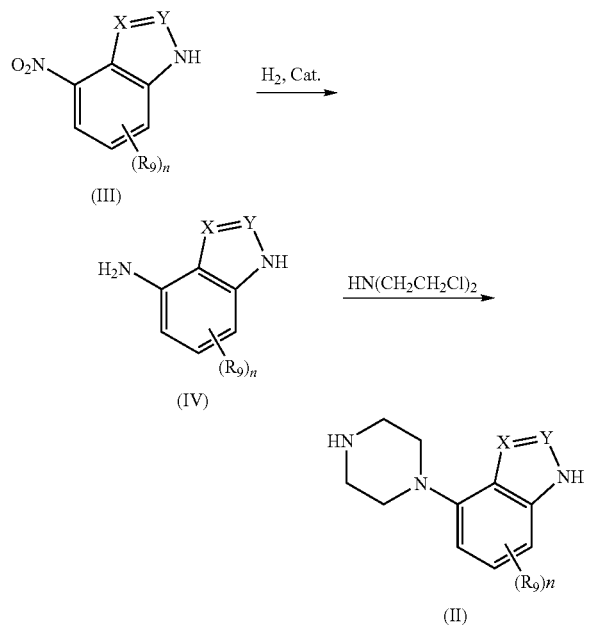

The formula II intermediate may then be converted to a compound of formula I wherein A is N, m is 2; $R_1$ is H; $R_2$, $R_3$, and $R_4$ are H; === represents a single bond; and the heterocyclyl group is in the 4-position, by reacting the formula II intermediate with a protecting group, G, for example di-t-butyl dicarbonate, to selectively protect the piperazine basic N atom to give the compound of formula V and sequentially reacting said formula V compound with a base such as NaH and a sulfonyl chloride, $R_8SO_2Cl$ to give the protected 4-(piperazin-1-yl)-1-(substituted-sulfonyl)indole and deprotecting said indole to give the desired compound of formula Ia. Reaction of said formula Ia compound with a reagent $R_1$-Hal, wherein $R_1$ is defined hereinabove for formula I and Hal is Cl, Br or I in the presence of a base gives compounds of formula Ib wherein $R_1$ is other than H. The reaction sequence is shown in flow diagram II.

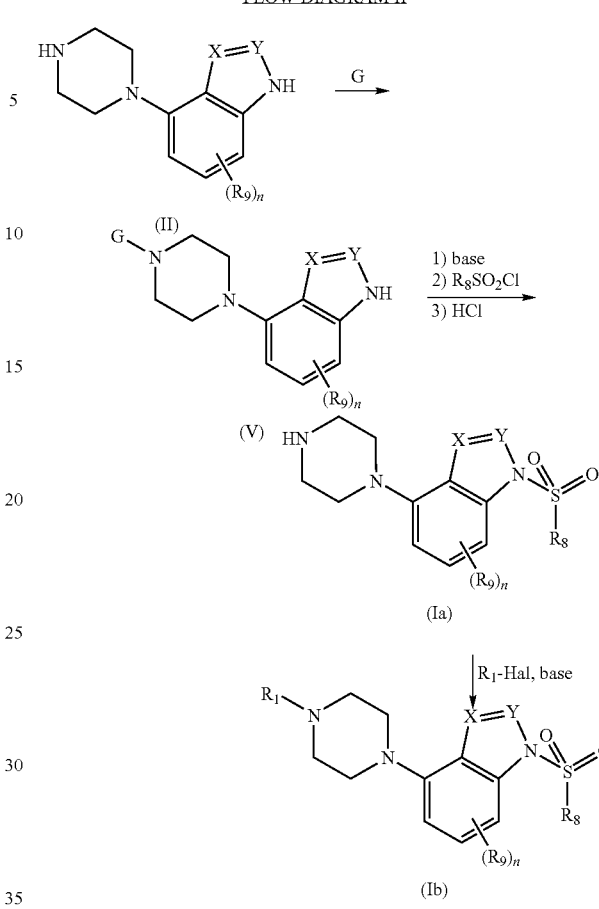

Corresponding compounds of the invention wherein A is $CR_{10}$ may be obtained, for example, by lithiating a protected 4-bromoindole of formula VI wherein G is benzyl, and displacing the lithium group with a cyclic ketone such as an N-protected-4-piperidone to give the hydroxy intermediate of formula VII, which may then be dehydrated and sulfonylated in the manner described hereinabove to give the protected compound of formula VIII. Catalytic hydrogenation and simultaneous deprotection of said formula VIII compound gives the desired compounds of formula I wherein === represents a single bond (formula Id). The reaction sequence is shown in flow diagram III.

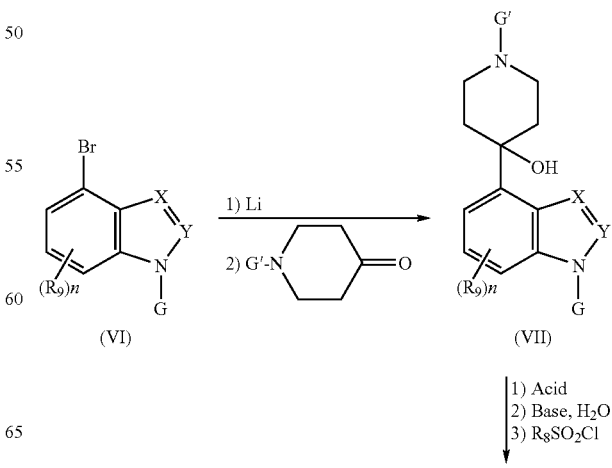

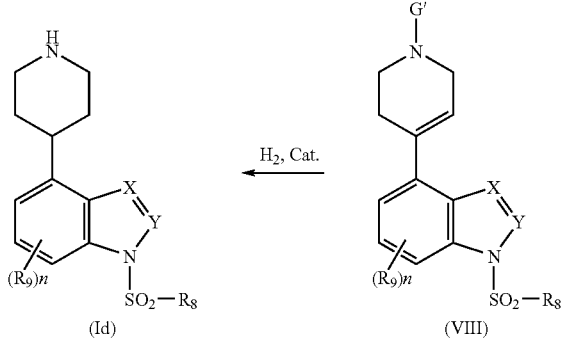

These and other literature procedures may be utilized to prepare the formula I compounds of the invention. Employing a 5-, 6- or 7-haloindole, -haloindazole or -halobenzimidazole substrate as starting material and using essentially the same procedures illustrated in flow diagrams I, II and III hereinabove enables the construction of the corresponding compounds of formula I wherein the heterocyclyl group is in the 5-, 6-, or 7-position and X or Y is N.

Advantageously, the inventive compound of formula I may be utilized in the treatment of central nervous system disorders relating to or affected by the 5-HT6 receptor such as motor, mood, psychiatric, cognitive, neurodegenerative or the like disorders. Accordingly, the present invention provides a method for the treatment of a disorder of the central nervous system (CNS) related to or affected by the 5-HT6 receptor in a patient in need thereof which comprises administering to said patient a therapeutically effective amount of a compound of formula I as described hereinabove. The compounds may be administered orally or parenterally or in any common manner known to be an effective administration of a therapeutic agent to a patient in need thereof.

The therapeutically effective amount administered in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are administered in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aids, binders, tablet-disintegrating agents or encapsulating materials. In powders, the carrier may be a finely divided solid which is in admixture with a finely divided compound of formula I. In tablets, the formula I compound is mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The terms HPLC and NMR designate high performance liquid chromatography and nuclear magnetic resonance, respectively.

EXAMPLE 1

Preparation of 1-(Phenylsulfonyl)-4-piperazin-1-yl-1H-indole Hydrochloride

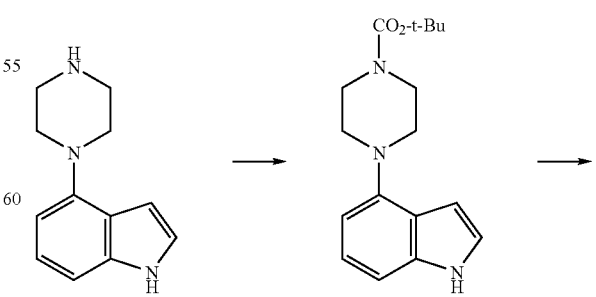

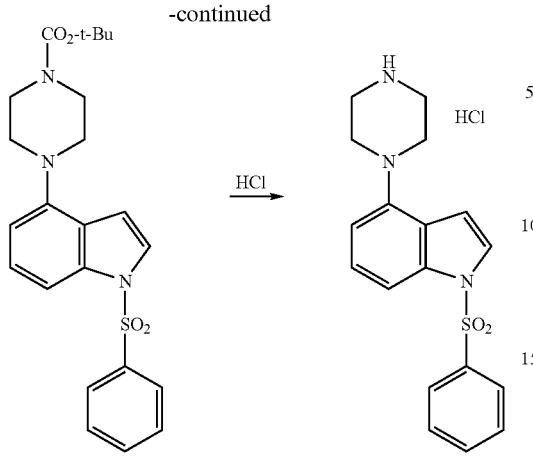

A mixture of 1H-indol-4-ylpiperazine (4.0 g, 20 mmol), di-t-butyl dicarbonate (4.8 g, 22 mmol) and NaOH (0.8 g, 20 mmol) in 40% dioxane is stirred at room temperature for 10 hours and treated with water. The reaction mixture is extracted with ethyl acetate. The extracts are combined, dried over $Na_2SO_4$ and concentrated in vacuo to give t-butyl 4-(1H-indol-4-yl)piperazine-1-carboxylate as a colorless solid, mp 137° C., identified by mass spectral and elemental analyses.

A portion of the t-butyl 4-(1H-indol-1-yl)-piperazine-1-carboxylate (1.05 g, 3.5 mmol) is added to a suspension of NaH (3.8 mmol) in tetrahydrofuran at 0° C. under $N_2$. The resultant mixture is stirred for 0.5 hr, treated with benzenesulfonyl chloride (0.616 g, 3.5 mmol), stirred for 16 hr and treated with water. The aqueous reaction mixture is extracted with ethyl acetate. The extracts are combined, dried over $Na_2SO_4$ and concentrated in vacuo to give a residue. The residue is chromatographed ($SiO_2$, $CH_2Cl_2$) to give t-butyl 4-(1-phenylsulfonyl-(1H-indol-4-yl)piperazine-1-carboxylate as a light yellow solid, 1.25 g (81% yield), mp 64-65° C., identified by mass spectral and elemental analyses.

A portion of the t-butyl 4-(1-benzenesulfonyl-1H-indol-4-yl)piperazine-1-carboxylate (0.85 g) is stirred in a mixture of 4N HCl and dioxane at room temperature for 2 hrs and filtered. The filtercake is dried to give the title product as a while solid, 0.64 g (99% yield) mp 60° C. identified by mass spectral and NMR analyses.

EXAMPLES 2-13

Preparation of
1-Arylsulfonyl-4-Piperazin-1-yl)-1H-Indole Hydrochloride

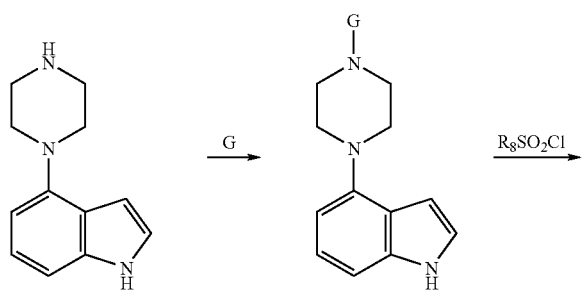

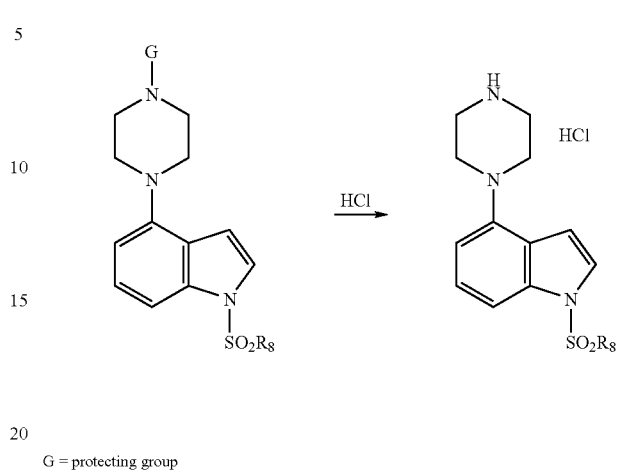

G = protecting group

Using essentially the same procedure described in Example 1 and substituting the appropriate arylsulfonyl chloride, the following compounds listed in Table I are obtained and identified by HPLC and mass spectral analyses.

TABLE I

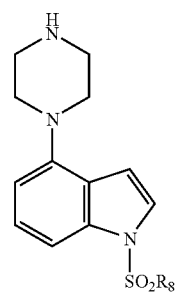

| Ex. No. | $R_8$ | LCMS[1] | |
|---|---|---|---|
| | | Min. | M + H |
| 2 | o-bromophenyl | 2.58 | 422 |
| 3 | 6-chloroimidazo[2,1-b]thiasol-5-yl | 2.48 | 422 |
| 4 | 3,4-dimethoxyphenyl | 2.52 | 402 |
| 5 | 4-aminophenyl | 2.26 | 357 |
| 6 | benzo-2,1,3-thiazol-4-yl | | |
| 7 | benzofurazan-4-yl | | |
| 8 | 3-bromo-5-chlorothien-2-yl | | |
| 9 | 5-chloro-3-methylbenzo(b)thien-2-yl | | |
| 10 | Dansyl | | |
| 11 | 2,5-dichlorothien-3-yl | | |
| 12 | 3,5-dimethylisoxasol-4-yl | | |
| 13 | 1-methylimidazol-4-yl | | |

[1]LCMS conditions: Hewlett Packard 1100 MSD; YMC ODS-AM 2.0 mm × 50 mm 5 u colunm at 23° C.; 3 uL injection; Solvent A: 0.02% TFA/water; Solvent B: 0.02% TFA/acetonitrile; Gradient: Time 0:95% A; 0.3 min: 95% A; 4.7 min: 10% A, 4.9 min: 95% A; Post time 1 min. Flow rate 1.5 mL/min; Detection: 254 nm DAD; API-ES Scanning Mode Positive 150-700; Fragmentor 70 mV.

EXAMPLE 14

Preparation of 4-[4-(4,5-Dihydro-1H-imidazol-2-yl)-piperazin-1-yl]-1-(phenylsulfonyl)-1H-indole

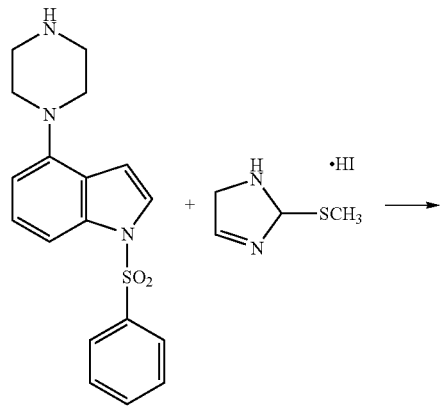

A solution of 1-(phenylsulfonyl)-4-piperzin-1-yl-1H-indole (71 mg, 0.18 mmol) in dioxane is treated with 2-methylthio-2-imidazoline hydroiodide (52.7 mg, 0.22 mmol) and N,N-diisopropylethylamine (62 μl, 0.36 mmol), heated at 50° C. for 16 hr., cooled and concentrated in vacuo to give a residue. The residue is purified by HPLC to give the title product, 15 mg, identified by HPLC and mass spectral analyses (2.57 min; 410 M+H) using the LCMS conditions described in Table I.

EXAMPLES 15-18

Preparation of 4-Heterocyclyl-1-(arylsulfonyl)indole compounds

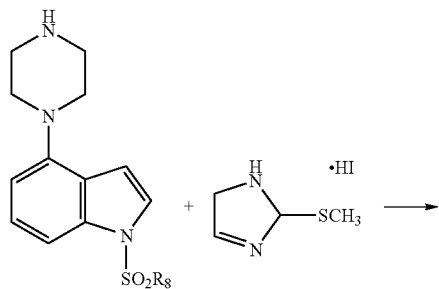

-continued

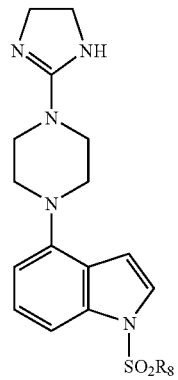

Using essentially the same procedure described in Example 14 and substituting the appropriate 1-(arylsulfonyl)indole substrate, the following compounds shown in Table II are obtained and identified by HPLC and mass spectral analyses.

TABLE II

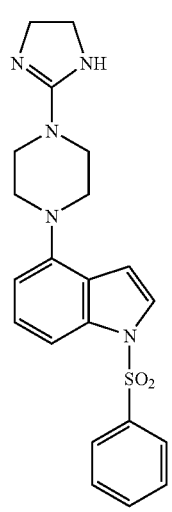

| Ex. No. | $R_8$ | LCMS[1] Min. | M + H |
|---|---|---|---|
| 15 | 2-bromophenyl | 2.79 | 490 |
| 16 | 6-chloroimidazo[2,1-b]thiazol-5-yl | 2.68 | 490 |
| 17 | 3,4-dimethoxyphenyl | 2.64 | 470 |
| 18 | 4-aminophenyl | 2.46 | 425 |

[1]LCMS conditions: same as for Table I

EXAMPLE 19

Preparation of 4-(4-Benzylpiperazin-1-yl)-1-(phenylsulfonyl)-1H-indole

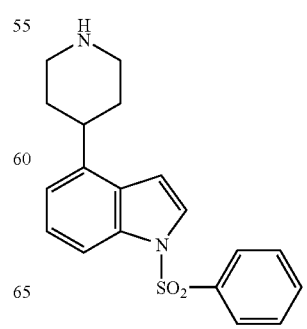

+

-continued

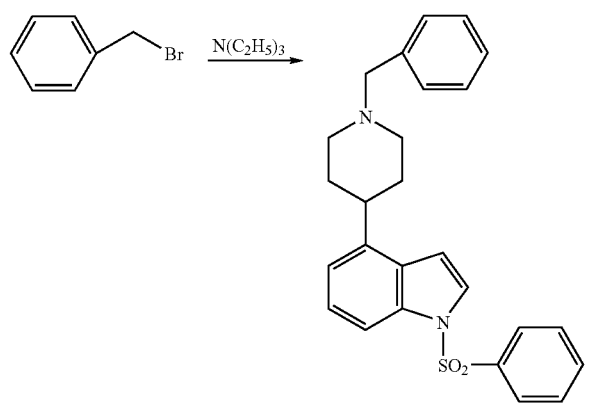

A solution of 1-(phenylsulfonyl)-4-piperazin-1-yl-1H-indole (71 mg, 0.18 mmol) in tetrahydrofuran is treated sequentially with benzyl bromide (21 µl) and triethyl-amine (75 µl), shaken at room temperature for 16 hr and concentrated in vacuo to give a residue. The residue is purified by RP-HPLC to give the title product, 37 mg, identfied by HPLC and mass spectral analyses (2.81 min; 432 M+H) using the LCMS conditions described in Table I.

EXAMPLES 20-53

Preparation of 4-Heteroaryl-1-arylsulfonylindole compounds

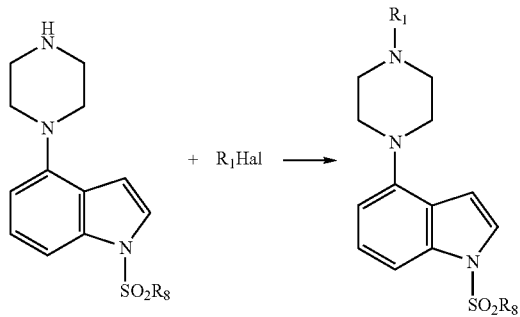

Using essentially the same procedure described in Example 19 and employing the appropriate 4-(piperazin-1-yl)-1-(arylsulfonyl)indole substrate and a suitable aryl, alkyl or acyl halide, the following compounds shown in Table III are obtained and identified by HPLC and mass spectral analyses.

TABLE III

| Ex. No. | $R_1$ | $R_8$ | LCMS[1] Min. | M + H |
|---|---|---|---|---|
| 20 | 2-chloro-5-thienylmethyl | phenyl | 3.07 | 472 |
| 21 | 3-nitrobenzyl | phenyl | 2.95 | 477 |
| 22 | Acetyl | phenyl | 3.18 | 384 |
| 23 | Benzyl | 2-bromophenyl | 2.99 | 512 |
| 24 | 2-chloro-5-thienylmethyl | 2-bromophenyl | 3.08 | 550 |
| 25 | 3-nitrobenzyl | 2-bromophenyl | 3.08 | 550 |
| 26 | Acetyl | 2-bromophenyl | 2.97 | 557 |
| 27 | Benzyl | 6-choroimidazol[2,1-b]thiazol-5-yl | 2.91 | 512 |
| 28 | 2-chloro-5-thienylmethyl | 6-choroimidazol[2,1-b]thiazol-5-yl | 3.00 | 553 |
| 29 | 3-nitrobenzyl | 6-choroimidazol[2,1-b]thiazol-5-yl | 2.87 | 557 |
| 30 | Acetyl | 6-choroimidazol[2,1-b]thiazol-5-yl | 3.23 | 464 |
| 31 | Benzyl | 3,4-dimethoxyphenyl | 2.76 | 492 |
| 32 | 2-chloro-5-thienylmethyl | 3,4-dimethoxyphenyl | 2.90 | 532 |
| 33 | 3-nitrobenzyl | 3,4-dimethoxyphenyl | 2.82 | 537 |
| 34 | Acetyl | 3,4-dimethoxyphenyl | 3.10 | 442 |
| 35 | benzyl | 4-aminophenyl | 2.64 | 447 |
| 36 | methyl | 4-aminophenyl | 2.28 | 371 |
| 37 | 2-chloro-5-thienylmethyl | 4-aminophenyl | 2.82 | 487 |
| 38 | 3-nitrobenzyl | 4-aminophenyl | 2.72 | 492 |
| 39 | 3-methoxybenzyl | Phenyl | 2.88 | 462 |
| 40 | 4-pyridylmethyl | Phenyl | 2.40 | 433 |
| 41 | 3-pyridylmethyl | Phenyl | 2.42 | 433 |
| 42 | 3-methoxybenzyl | 2-bromophenyl | 2.99 | 542 |
| 43 | 4-pyridylmethyl | 2-bromophenyl | 2.51 | 513 |
| 44 | 3-pyridylmethyl | 2-bromophenyl | 2.52 | 513 |
| 45 | 3-methoxybenzyl | 6-chloroimidazo[2,1-b]thiazol-5-yl | 2.93 | 542 |
| 46 | 4-pyridylmethyl | 6-chloroimidazo[2,1-b]thiazol-5-yl | 2.48 | 513 |
| 47 | 3-pyridylmethyl | 6-chloroimidazo[2,1-b]thiazol-5-yl | 2.48 | 513 |
| 48 | 3-methoxybenzyl | 3,4-dimethoxyphenyl | 2.82 | 522 |
| 49 | 4-pyridylmethyl | 3,4-dimethoxyphenyl | 2.47 | 493 |
| 50 | 3-pyridylmethyl | 3,4-dimethoxyphenyl | 2.45 | 493 |
| 51 | 3-methoxybenzyl | 4-aminophenyl | 2.75 | 477 |
| 52 | 4-pyridylmethyl | 4-aminophenyl | 2.24 | 448 |
| 53 | 3-pyridylmethyl | 4-aminophenyl | 2.26 | 448 |

[1]LCMS conditions are the same as that for Table I

EXAMPLE 54

Preparation of 4-(Homopiperazin-1-yl)-1-(phenylsulfonyl)-benzimidazole hydrochloride

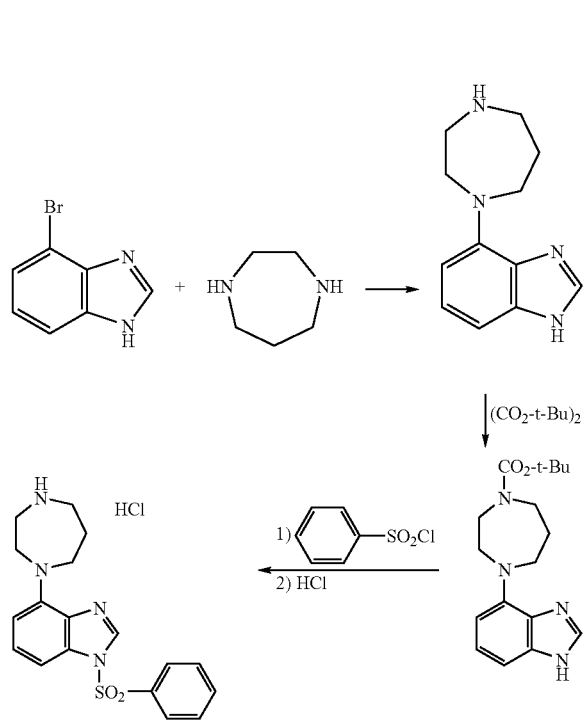

A suspension of 4-bromobenzimidazole (42 mmol), homopiperazine (256 mmol) and NaOt-Bu (59 mmol) in dry o-xylene, under N₂, is treated with a catalytic amount of Pd(OCOCH₃)₂·P(t-Bu)₃ (P/Pd=4), heated at 120° C. for 3 hr, cooled to room temperature and diluted with water. The aqueous mixture is extracted with ethyl acetate. The extracts are combined, dried over MgSO₄ and concentrated in vacuo to give a residue. The residue is purified by flash chromatography to give 4-(homopiperazin-1-yl)benzimidazole.

A mixture of 4-(homopiperazin-1-yl)benzimidazole (4.3 g, 20 mmol), di-t-butyl dicarbonate (4.8 g, 22 mmol) and NaOH (0.8 g, 20 mmol) in 40% aqueous dioxane is stirred at room temperature for 10 hrs and diluted with water. The aqueous mixture is extracted with ethyl acetate. The extracts are combined, dried over NaSO₄ and concentrated in vacuo to give t-butyl 4-(benzimidazol-4-yl)homopiperazine-1-carboxylate.

A suspension of NaH (3.8 mmol) in tetrahydrofuran at 0° C., under N₂, is treated with t-butyl 4-(benzimidazol-4-yl)-homopiperazine-1-carboxylate (1.1 g, 3.5 mmol), stirred for 0.5 hr, treated with benzenesulfonyl chloride (0.616 g, 3.5 mmol), stirred for 16 hours at room temperature and diluted with water. The aqueous mixture is extracted with ethyl acetate. The extracts are combined, dried over Na₂SO₄ and concentrated in vacuo to give a residue. The residue is purified by flash chromatography to give t-butyl 4-(1-phenylsulfonyl)-benz-imidazol-4-yl)homopiperazin-1-carboxylate.

A mixture of the thus-obtained carboxylate in 4N HCl and dioxane is stirred at room temperature for 2 hrs and filtered. The filtercake is washed with ethyl acetate and dried in vacuo to afford the title product.

EXAMPLE 56

Preparation of 4-(4-Benzylpiperazin-1-yl)-1H-indazole

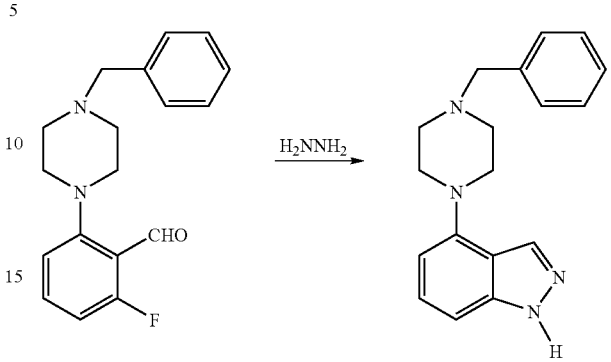

A stirred solution of 4-benzyl-1-(3-fluoro-2-carboxyphenyl)-piperazine (5.96 g, 20.0 mmol) in dimethylsulfoxide (10 mL) and hydrazine (10 mL) is heated at 95° C. under nitrogen for 4 days. The cooled reaction is diluted with ether and washed with a mixture of water and saturated aqueous sodium bicarbonate. The organic layer is further washed sequentially with water and brine dried over MgSO₄ and concentrated in vacuo to give a residue. The residue is chromatographed using ethyl acetate as the eluant. The resulting oil is reconcentrated from ether to give a white foam which is stirred under hexanes/ether overnight. The resulting white powder is isolated by suction filtration and washed with hexane to give the title compound 3.11 g, (53% yield), identified by HNMR.

EXAMPLE 57

Preparation of 4-(4-Benzylpiperazin-1-yl)-1-(phenylsulfonyl)-1H-indazole hydrochloride

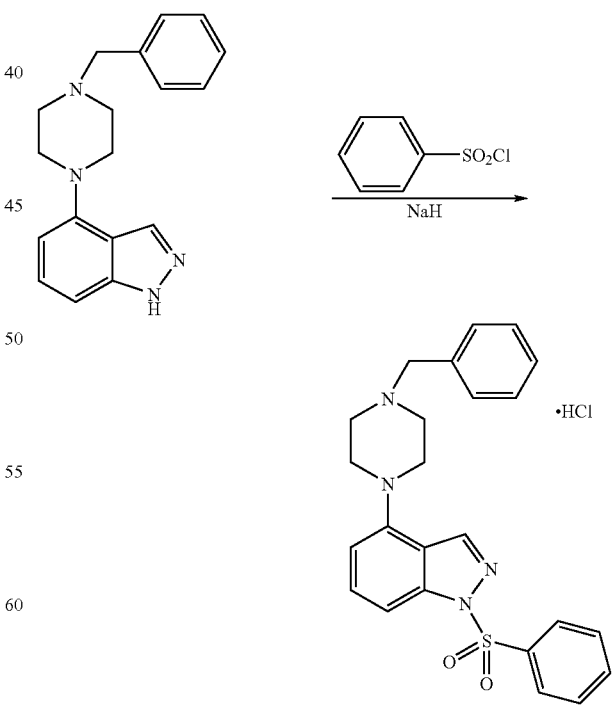

A solution of 4-(4-benzylpiperazin-1-yl)-1H-indazole (2.34 g, 8.00 mmol) in dry dimethyl formamide is treated with 0.48 g unwashed 60% NaH in mineral oil (12.0 mmol of NaH). After stirring under nitrogen for 15 min, the reaction is treated with benzenesulfonylchloride (1.53 mL, 12.0 mmol), stirred for 24 hr at ambient temperature, treated with saturated aqueous NaHCO₃ and water and extracted with ether. The organic layer is washed sequentially with water and brine, dried over MgSO₄ and concentrated in vacuo to give a residue. The residue is purified by flash chromatography on silica gel using 1:1 ethyl acetate:hexanes as eluant to afford the free amine of the title compound as an oil (3.14 g, 91%). A portion of this oil (432 mg, 1.0 mmol) is dissolved in ether and treated with 1.0M HCl in ether (1.1 mL, 1.1 mmol). The resulting solid is filtered, washed with ether, and dried under vacuum to provide the title compound as a light tan solid, mp 208-209° C., identified by HNMR and mass spectral analyses.

EXAMPLE 58

Preparation of 1-(Phenylsulfonyl)-4-(1-piperazinyl)-1H-indazole hydrochloride

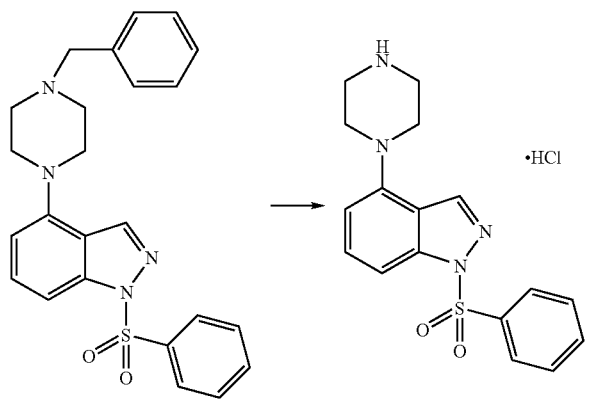

A solution of 1-phenylsulfonyl-4-(4-benzylpiperazin-1-yl)-1H-indazole (433 mg, 1.0 mmol) in 1,2-dichloroethane is treated with 1-chloroethyl chloroformate (0.27 mL, 2.5 mmol) heated at reflux temperature for 2 hr, and concentrated in vacuo. The resultant residue is heated at reflux temperature in methanol for 1.5 hr, cooled, concentrated in vacuo and reconcentrated from ether. The resulting tan solid is triturated with ether and crystallized from hot ethanol to give the title compound as a tan solid 237 mg (63% yield), mp 203-205° C., identified by HNMR and mass spectral analyses.

EXAMPLE 59

Preparation of 4-[4-(2-phenylethyl)piperazin-1-yl]-1-(phenylsulfonyl)-1H-indazole hydrochloride

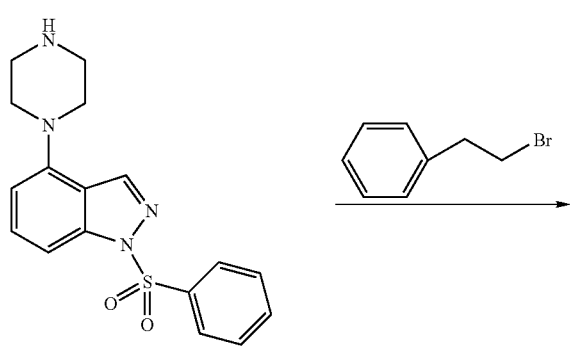

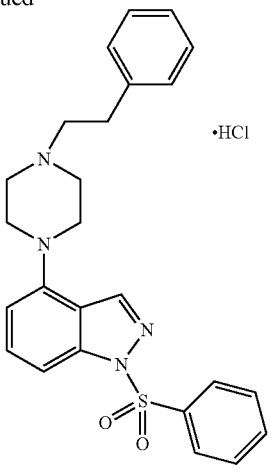

A mixture of 1-phenylsulfonyl-4-piperazin-1-yl-1H-indazole (190 mg, 0.50 mmol) and K₂CO₃ (138 mg, 1.0 mmol) in dry acetonitrile is treated with phenethylbromide (0.55 mL, 2.0 mmol), heated at reflux temperature under nitrogen for 8.5 h, treated with water and extracted with methylene chloride. The combined extracts are dried over MgSO₄ and chromatographed on an SCX column (Varian SCX Mega Bond Elut, 5 g) eluting with ethyl acetate to remove non-basic organic material and then with 1:99 triethylamine:ethyl acetate to afford, after concentration, the free amine of the title compound as a slightly yellow oil (198 mg, 89%). The oil is dissolved in ether with a small amount of ethanol to aid solubility and treated with 1.0M HCl in ether. The solution is concentrated in vacuo and the resulting tan solid is treated with ether and suction filtered to afford the title compound as a light tan solid 209 mg, (87% yield), mp 230-232° C. (dec), identified by NMR and mass spectral analyses.

EXAMPLES 60-72

Preparation of 4-Heteroaryl-1-arylsulfonylindazole compounds

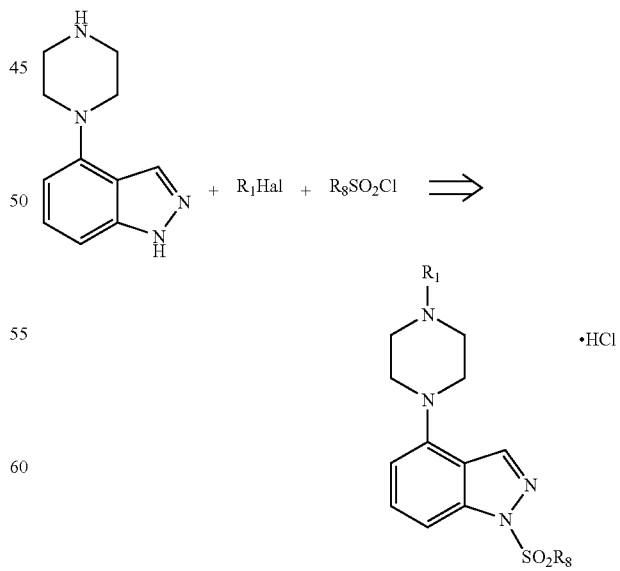

Using essentially the same procedures described in Examples 56-59 and employing the appropriate indazole substrate and suitable aryl, alkyl or acyl halide or arylsulfonyl chloride, the following compounds shown in Table IV are obtained and identified by NMR and mass spectral analyses.

TABLE IV

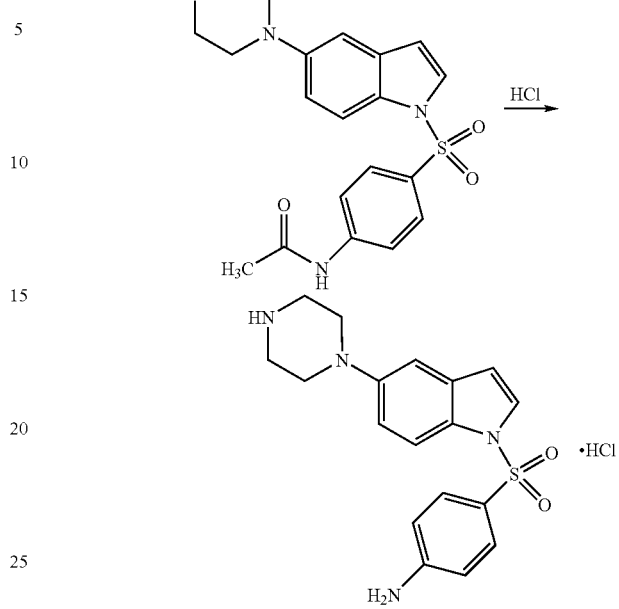

| Ex. No. | R$_1$ | R$_8$ | mp °C. | M+H |
|---|---|---|---|---|
| 60 | 2(p-fluorophenoxy)ethyl- | Phenyl | 184-186 | 481 |
| 61 | p-flourophenyl-CO—(CH$_2$)$_3$— | Phenyl | — | 507 |
| 62 | phenyl-CO—CH$_2$— | phenyl | 202-205 | 461 |
| 63 | 3-phenylpropyl- | phenyl | 188-190 | 461 |
| 64 | n-propyl- | phenyl | 258-260 | 385 |
| 65 | benzyl | phenyl-CH=CH— | 233-235 | 459 |
| 66 | benzyl | p-fluorophenyl | 240-241 | 451 |
| 67 | benzyl | p-chlorophenyl | 238-239 | 467 |
| 68 | benzyl | naphthyl | 147-149 | 483 |
| 69 | benzyl | p-methoxyphenyl | 206-209 | 463 |
| 70 | benzyl | p-(trifluoromethoxy)phenyl | 229-231 | 517 |
| 71 | benzyl | 2-(4,5-dichlorothienyl)- | 235-237 | 507 |
| 72 | benzyl | p-tolyl | 215-217 | 447 |

EXAMPLE 73

Preparation of 1-(4-Aminophenylsulfonyl)-5-piperazin-1-yl-1H-indole hydrochloride

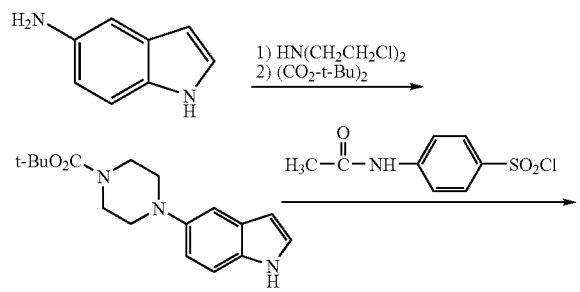

A solution of 5-aminoindole (6.23 g, 47 mmol), bis(2-chloroethyl)amine hydrochloride (16.8 g, 96 mmol) and triethylamine (19 mL, 141 mmol) in butanol is heated at 100° C. for 8 hours, cooled to room temperature and concentrated in vacuo to give 9.46 g of 5-piperazin-1-yl-1H-indole.

A solution of said indole in acetone and water is treated with di-tert-butyl dicarbonate (11.3 g, 47 mmol) and potassium carbonate (13 g, 96 mmol). The mixture is stirred at room temperature overnight, the acetone evaporated and the remaining aqueous phase extracted with ethyl acetate. The extracts are dried over MgSO$_4$ and concentrated in vacuo to give a residue. The residue is purified by flash chromatography to give 4-(1H-indol-5-yl)-piperazine-1-carboxylic acid tert-butyl ester.

A solution of said ester (60 mg, 0.2 mmol) in tetrahydrofuran is treated with sodium hydride (30 mg, 0.5 mmol) followed by N-acetylsulfanilyl chloride (25 uL, 0.2 mmol), shaken at room temperature for 16 hours and concentrated in vacuo to give 4-[1-(4-acetylaminophenylsulfonyl)-1H-indol-5-yl]-piperazine-1-carboxylic acid tert-butyl ester.

The thus-obtained ester is dissolved in methanol, treated with concentrated hydrochloric acid (100 uL), shaken at 60° C. for 2 hours and concentrated in vacuo to give a residue. The residue is purified by HPLC to give the title product, 15 mg, identified by HPLC and mass spectral analyses (r.t. 2.37 min., M+H 357).

EXAMPLES 74-102

Preparation of Piperazinyl-1-arylsulfonylindazole and indole compounds

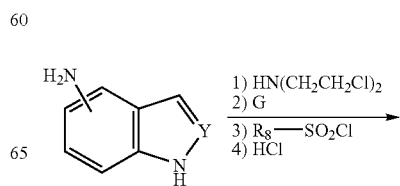

-continued

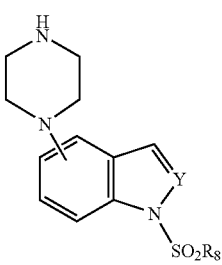

G = protecting group

Using essentially the same procedures described in Example 73 and employing the appropriate aminoindole or aminoindazole substrate and suitable arylsulfonylchloride reagents, the following compounds shown in Table V are obtained and identified by HPLC and mass spectral analyses.

TABLE V

| Ex. No. | Piperazinyl Ring Position | Y | R$_8$ | LCMS[1] Min. | M + H |
|---|---|---|---|---|---|
| 74 | 5 | N | phenyl | 1.98 | 343 |
| 75 | 6 | N | phenyl | 1.96 | 343 |
| 76 | 5 | CH | benzo-2,1,3-thiadiazol-4-yl | 2.56 | 400 |
| 77 | 6 | N | benzo-2,1,3-thiadiazol-4-yl | 2.01 | 401 |
| 78 | 6 | N | 2-bromophenyl | 2.21 | 423 |
| 79 | 5 | N | p-bromophenyl | 2.39 | 423 |
| 80 | 6 | N | p-bromophenyl | 2.34 | 423 |
| 81 | 5 | N | 5-bromothien-2-yl | 2.33 | 429 |
| 82 | 6 | N | 5-bromothien-2-yl | 2.25 | 429 |
| 83 | 5 | CH | p-(n-butoxy)phenyl | 3.23 | 414 |
| 84 | 5 | N | p-(n-butoxy)phenyl | 2.79 | 415 |
| 85 | 6 | N | p-(n-butoxy)phenyl | 2.73 | 415 |
| 86 | 5 | CH | 5-chloro-1,3-dimethyl-pyrazol-4-yl | 2.49 | 395 |
| 87 | 5 | N | 5-chloro-1,3-dimethyl-pyrazol-4-yl | 1.88 | 396 |
| 88 | 5 | N | 5-chloro-3-methylbenzo-[b]thien-2-yl | 2.88 | 448 |
| 89 | 6 | N | 5-chloro-3-methylbenzo-[b]thien-2-yl | 3.10 | 448 |
| 90 | 5 | N | 2,3-dichlorothien-5-yl | 2.59 | 418 |
| 91 | 6 | N | 2,3,-dichlorothien-5-yl | 2.77 | 418 |
| 92 | 5 | N | p-fluorophenyl | 2.08 | 361 |
| 93 | 6 | N | p-fluorophenyl | 2.40 | 361 |
| 94 | 5 | N | p-methoxyphenyl | 2.11 | 373 |
| 95 | 5 | CH | 2-naphthyl | 2.92 | 392 |
| 96 | 6 | N | 2-naphthyl | 2.43 | 393 |
| 97 | 5 | CH | p-(trifluoromethoxy)phenyl | 2.97 | 426 |
| 98 | 5 | N | p-(trifluoromethoxy)phenyl | 2.57 | 427 |
| 99 | 6 | N | p-(trifluoromethoxy)phenyl | 2.54 | 427 |
| 100 | 5 | CH | p-iodophenyl | 2.92 | 468 |
| 101 | 5 | N | p-iodophenyl | 2.48 | 469 |
| 102 | 6 | N | p-iodophenyl | 2.67 | 469 |

EXAMPLE 103

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10-25 μl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 μl. To each well is added the following mixture: 80.0 μl of incubation buffer made in 50 mM Tris.HCl buffer (pH 7.4) containing 10.0 mM $MgCl_2$ and 0.5 mM EDTA and 20 μl of [$^3$H]-LSD (S.A., 86.0 Ci/mmol, available from Amersham Life Science), 3.0 nM. The dissociation constant, $K_D$ of the [$^3$H]LSD at the human serotonin 5-HT6 receptor is 2.9 nM, as determined by saturation binding with increasing concentrations of [$^3$H]LSD. The reaction is initiated by the final addition of 100.0 μl of tissue suspension. Nonspecific binding is measured in the presence of 10.0 μM methiothepin. The test compounds are added in 20.0 μl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 μl Microscint®-20 scintillant to each shallow well. The unifilter plate is heat-sealed and counted in a PackardTopCount® with a tritium efficiency of 31.0%.

Specific binding to the 5-HT6 receptor is defined as the total radioactivity bound less the amount bound in the presence of 10.0 μM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yielded both the $IC_{50}$ and the $K_i$ values of test compounds with 95% confidence limits. A linear regression line of data points is plotted, from which the $IC_{50}$ value is determined and the $K_i$ value is determined based upon the following equation:

$$K_i = IC_{50}/(1+L/K_D)$$

where L is the concentration of the radioactive ligand used and $K_D$ is the dissociation constant of the ligand for the receptor, both expressed in nM.

Using this assay, the following Ki values are determined and compared to those values obtained by representative compounds known to demonstrate binding to the 5-HT6 receptor. The data are shown in Table VI, below.

TABLE VI

| Test Compound (Ex. No.) | 5-HT6 binding Ki (nM) |
|---|---|
| 1 | 1.0 |
| 2 | 2.0 |
| 3 | 1.0 |
| 4 | 15.0 |
| 5 | 1.0 |
| 14 | 24.0 |
| 18 | 6.0 |
| 27 | 56.0 |
| 30 | 220.0 |
| 33 | 45.0 |
| 35 | 15.0 |
| 36 | 3.0 |
| 37 | 59.0 |
| 38 | 5.0 |
| 40 | 4.0 |
| 41 | 7.0 |
| 42 | 4.0 |
| 43 | 7.0 |
| 44 | 1.0 |
| 46 | 5.0 |
| 47 | 6.0 |
| 48 | 14.0 |
| 49 | 10.0 |
| 50 | 17.0 |
| 51 | 7.0 |
| 52 | 25.0 |
| 53 | 4.0 |
| 57 | 14 |
| 58 | 0.3 |
| 59 | 1.0 |
| 60 | 306 |
| 61 | 3.0 |
| 62 | 12 |
| 63 | 6.0 |
| 64 | 2.0 |
| 65 | 172 |
| 66 | 84 |
| 67 | 87 |
| 68 | 14 |
| 69 | 116 |
| 70 | 251 |
| 71 | 81 |
| 72 | 56 |
| 73 | 34 |
| 79 | 19 |
| 81 | 44 |
| 83 | 38 |
| 86 | 44 |
| 89 | 24 |
| 90 | 30 |
| 91 | 6 |
| 96 | 37 |
| 101 | 18 |
| Comparative Examples | |
| Clozapine | 6.0 |
| Loxapine | 41.4 |
| Bromocriptine | 23.0 |
| Methiothepin | 8.3 |
| Mianserin | 44.2 |
| Olanzepine | 19.5 |

As can be seen from the results set forth above, the compounds of the present invention have a high degree of affinity for the serotonin 5-HT6 receptor sub-type. Although two of the comparison compounds (clozapine and methiothepin) have similar 5-HT6 receptor affinity, they do not have the selectivity of the compounds of the present invention. The examples disclosed above demonstrate up to 50-fold selectivity for the 5-HT6 receptor when compared to their affinity at the 5-HT7 receptor.

What is claimed is:

1. A compound of formula I

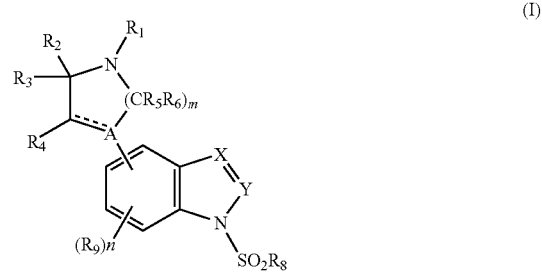

wherein
A is N;
X is N;
Y is CH;
$R_1$ is H or $C_1$-$C_4$ alkyl substituted with 0-3 of halogen, hydroxyl, $C_1$-$C_4$ alkoxy, $C_1$-$C_4$ alkyl, $C_1$-$C_4$ haloalkyl, $C_1$-$C_4$ haloalkoxy or combinations thereof;
$R_2$, $R_3$, $R_4$, $R_5$ and $R_6$ are each independently H, halogen, OH or a $C_1$-$C_6$ alkyl group;
$R_8$ is phenyl or naphthyl each substituted with 0-3 of halogen, hydroxyl, $C_1$-$C_4$ alkoxy, $C_1$-$C_4$ alkyl, $C_1$-$C_4$ haloalkyl, $C_1$-$C_4$ haloalkoxy or combinations thereof;
$R_9$ is H;
m is an integer of 3;
n is 0 or an integer of 1, 2 or 3; and
---- represents a single bond; or
a pharmaceutically acceptable salt thereof.

2. A compound of the following formula:

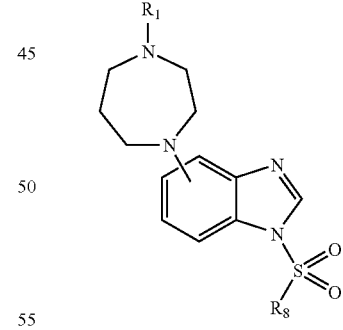

wherein
$R_1$ is H or $C_1$-$C_4$ alkyl substituted with 0-3 of halogen, hydroxyl, $C_1$-$C_4$ alkoxy, $C_1$-$C_4$ alkyl, $C_1$-$C_4$ haloalkyl, $C_1$-$C_4$ haloalkoxy or combinations thereof;
$R_8$ is phenyl or naphthyl each substituted with 0-3 of halogen, hydroxyl, $C_1$-$C_4$ alkoxy, $C_1$-$C_4$ alkyl, $C_1$-$C_4$ haloalkyl, $C_1$-$C_4$ haloalkoxy or combinations thereof; or
a pharmaceutically acceptable salt thereof.

3. The compound according to claim 2, wherein $R_1$ is H or $C_1$-$C_4$ alkyl.

4. The compound according to claim 3, wherein $R_1$ is H.

5. The compound according to claim 2, wherein $R_8$ is phenyl substituted with 0-3 of halogen, hydroxyl, $C_1$-$C_4$ alkoxy, $C_1$-$C_4$ alkyl, $C_1$-$C_4$ haloalkyl, $C_1$-$C_4$ haloalkoxy or combinations thereof.

6. The compound according to claim 2, wherein the compound is selected from:
4-(homopiperazin-1yl)-1-(phenylsulfonyl)-benzimidazole or a pharmaceutically acceptable salt thereof.

7. A method for the treatment of a disorder of the central nervous system related to or affected by the 5-HT6 receptor selected from anxiety disorder, schizophrenia, depression, or attention deficit disorder in a patient in need thereof which comprises administering to said patient a therapeutically effective amount of a compound of the following formula:

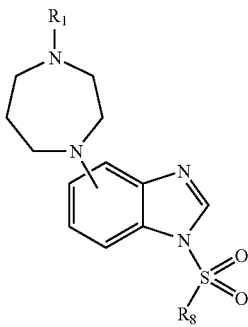

wherein
$R_1$ is H or $C_1$-$C_4$ alkyl substituted with 0-3 of halogen, hydroxyl, $C_1$-$C_4$ alkoxy, $C_1$-$C_4$ alkyl, $C_1$-$C_4$ haloalkyl, $C_1$-$C_4$ haloalkoxy or combinations thereof;
$R_8$ is phenyl or naphthyl each substituted with 0-3 of halogen, hydroxyl, $C_1$-$C_4$ alkoxy, $C_1$-$C_4$ alkyl, $C_1$-$C_4$ haloalkyl, $C_1$-$C_4$ haloalkoxy or combinations thereof; or a pharmaceutically acceptable salt thereof.

8. The method according to claim 7, wherein said disorder is a anxiety disorder.

9. The method according to claim 7, wherein said disorder is schizophrenia.

10. The method according to claim 7, wherein said disorder is an attention deficit disorder.

11. The method according to claim 7, wherein said disorder is depression.

12. A pharmaceutical composition which comprises a pharmaceutically acceptable carrier and an effective amount of a compound of the following formula:

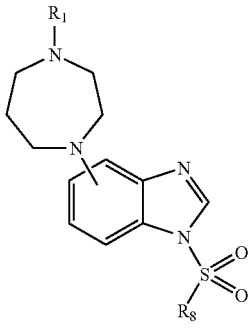

wherein
$R_1$ is H or $C_1$-$C_4$ alkyl substituted with 0-3 of halogen, hydroxyl, $C_1$-$C_4$ alkoxy, $C_1$-$C_4$ alkyl, $C_1$-$C_4$ haloalkyl, $C_1$-$C_4$ haloalkoxy or combinations thereof;

$R_8$ is phenyl or naphthyl each substituted with 0-3 of halogen, hydroxyl, $C_1$-$C_4$ alkoxy, $C_1$-$C_4$ alkyl, $C_1$-$C_4$ haloalkyl, $C_1$-$C_4$ haloalkoxy or combinations thereof; or a pharmaceutically acceptable salt thereof.

13. The composition according to claim 12, wherein $R_1$ is H or $C_1$-$C_4$ alkyl.

14. The composition according to claim 13, wherein $R_1$ is H.

15. The composition according to claim 12, wherein $R_8$ is phenyl substituted with 0-3 of halogen, hydroxyl, $C_1$-$C_4$ alkoxy, $C_1$-$C_4$ alkyl, $C_1$-$C_4$ haloalkyl, $C_1$-$C_4$ haloalkoxy or combinations thereof.

16. The composition according to claim 12, wherein the compound is selected from:
4-(homopiperazin-1yl)-1-(phenylsulfonyl)-benzimidazole or a pharmaceutically acceptable salt thereof.

17. A method for the preparation of a compound of the following formula:

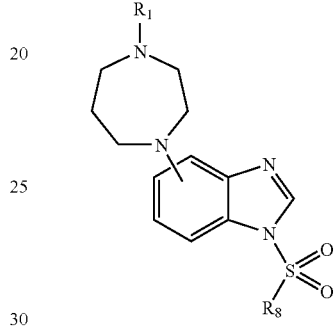

wherein
$R_1$ is H or $C_1$-$C_4$ alkyl substituted with 0-3 of halogen, hydroxyl, $C_1$-$C_4$ alkoxy, $C_1$-$C_4$ alkyl, $C_1$-$C_4$ haloalkyl, $C_1$-$C_4$ haloalkoxy or combinations thereof;
$R_8$ is phenyl or naphthyl each substituted with 0-3 of halogen, hydroxyl, $C_1$-$C_4$ alkoxy, $C_1$-$C_4$ alkyl, $C_1$-$C_4$ haloalkyl, $C_1$-$C_4$ haloalkoxy or combinations thereof; or a pharmaceutically acceptable salt thereof;
said method which comprises reacting a compound of the following formula:

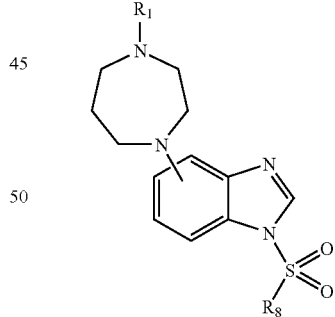

with a compound $R_1$-Hal, wherein $R_1$ and $R_8$ are as defined hereinabove and Hal is Cl, Br or I.

18. The method according to claim 7, wherein $R_1$ is H or $C_1$-$C_4$ alkyl.

19. The method according to claim 7, wherein $R_1$ is H.

20. The method according to claim 7, wherein $R_8$ is phenyl substituted with 0-3 of halogen, hydroxyl, $C_1$-$C_4$ alkoxy, $C_1$-$C_4$ alkyl, $C_1$-$C_4$ haloalkyl, $C_1$-$C_4$ haloalkoxy or combinations thereof.

* * * * *